United States Patent
Roy et al.

(10) Patent No.: US 10,889,854 B2
(45) Date of Patent: Jan. 12, 2021

(54) SYSTEM AND METHOD FOR IMMOBILIZATION FREE ELECTROCHEMILUMINESCENCE DNA DETECTION USING A LUMINOPHORE DYE FOR MULTI-SPECIES DETECTION

(71) Applicant: Universiti Brunei Darussalam, Gadong (BN)

(72) Inventors: Sharmili Roy, Gadong (BN); Minhaz Uddin Ahmed, Gadong (BN)

(73) Assignee: UNIVERSITI BRUNEI DARUSSALAM, Gadong (BN)

( * ) Notice: Subject to any disclaimer, the term of this patent is extended or adjusted under 35 U.S.C. 154(b) by 179 days.

(21) Appl. No.: 15/672,233

(22) Filed: Aug. 8, 2017

(65) Prior Publication Data
US 2018/0037944 A1 Feb. 8, 2018

(51) Int. Cl.
| | | |
|---|---|---|
| *C12Q 1/68* | (2018.01) | |
| *C12Q 1/6844* | (2018.01) | |
| *C12Q 1/689* | (2018.01) | |
| *C12Q 1/6881* | (2018.01) | |
| *C12Q 1/6816* | (2018.01) | |

(52) U.S. Cl.
CPC ........... *C12Q 1/6846* (2013.01); *C12Q 1/689* (2013.01); *C12Q 1/6816* (2013.01); *C12Q 1/6881* (2013.01)

(58) Field of Classification Search
None
See application file for complete search history.

(56) References Cited

U.S. PATENT DOCUMENTS

| | | | |
|---|---|---|---|
| 7,314,974 B2 * | 1/2008 | Cao | C07K 14/195 800/289 |
| 2011/0312819 A1 * | 12/2011 | Azimi | B01L 3/5027 506/39 |

OTHER PUBLICATIONS

Corbin et al. (J Mol Evol 2007, 65:403-412) (Year: 2007).*
Garcia et al. (Genet Mol Biol, 2011, 34(2):329-337) (Year: 2011).*
Workman et al. (Anal Chem, 2000, vol. 72, p. 5556-5561) (Year: 2000).*
Rooney et al. (Int J of Syst Evol. Micro, 2009, 59:2429-2436) (Year: 2009).*
Yuan et al. (Analytica Chimica Acta, 2014, 811:70-75) (Year: 2014).*
Yu et al. (J of Immunol Methods, 1998, 218:1-8) (Year: 1998).*
Chu et al. (Sensors, 2010, 10:9481-9492) (Year: 2010).*
Roy et al. Food Control, 2016, vol. 61, p. 70-78 (Year: 2016).*

* cited by examiner

*Primary Examiner* — Stephanie K Mummert
(74) *Attorney, Agent, or Firm* — Sinorica, LLC

(57) ABSTRACT

Present invention disclosed a novel method for detecting and quantifying target DNA from the biological sample. It provides a method of amplification of DNA sequences with loop-mediated isothermal amplification (LAMP) and its easy and accurate detection and quantification by electrochemiluminescence (ECL) technique. The target LAMP DNA is bound electrostatically with $[Ru(bpy)_3]^{+2}$ on the carbon electrode surface, and an ECL reaction is triggered by tripropylamine (TPrA) to yield luminescence. This is a highly sensitive strategy for the detection of sequence-specific DNA from different biological samples at picogram levels. The target DNA of *Sus scrofa* (pork) meat was detected as low as 1 pg/μL ($3.43 \times 10^{-1}$ copies/μL) and for *Bacillus subtilis* DNA samples the detection limit of 10 pg/μL ($2.2 \times 10^3$ copies/μL) was achieved.

15 Claims, 4 Drawing Sheets

Specification includes a Sequence Listing.

SEQUENCE LISTING

```
<160> NUMBER OF SEQ ID NOS: 12

<210> SEQ ID NO 1
<211> LENGTH: 18
<212> TYPE: DNA
<213> ORGANISM: Sus scrofa

<400> SEQUENCE: 1
tcgcctacgc tattctac                                                   18

<210> SEQ ID NO 2
<211> LENGTH: 21
<212> TYPE: DNA
<213> ORGANISM: Sus scrofa

<400> SEQUENCE: 2
ggaagtataa gatggaggct a                                               21

<210> SEQ ID NO 3
<211> LENGTH: 40
<212> TYPE: DNA
<213> ORGANISM: Sus scrofa

<400> SEQUENCE: 3
ggatgtgtgt agtatgggca ttaactaggt ggagtgttgg                           40

<210> SEQ ID NO 4
<211> LENGTH: 40
<212> TYPE: DNA
<213> ORGANISM: Sus scrofa

<400> SEQUENCE: 4
ttcgaccact aagtcaatgc cggttgtcct ccaattcatg                           40

<210> SEQ ID NO 5
<211> LENGTH: 22
<212> TYPE: DNA
<213> ORGANISM: Sus scrofa

<400> SEQUENCE: 5
```

```
attaggatta ggatggaggc ta                                              22

<210> SEQ ID NO 6
<211> LENGTH: 22
<212> TYPE: DNA
<213> ORGANISM: Sus scrofa

<400> SEQUENCE: 6
ctagtagcag acctcattac ac                                              22

<210> SEQ ID NO 7
<211> LENGTH: 22
<212> TYPE: DNA
<213> ORGANISM: Bacillus subtilis

<400> SEQUENCE: 7
gaagaggata tgccttacct tc                                              22

<210> SEQ ID NO 8
<211> LENGTH: 21
<212> TYPE: DNA
<213> ORGANISM: Bacillus subtilis

<400> SEQUENCE: 8
cgacagatac acggttatca a                                               21

<210> SEQ ID NO 9
<211> LENGTH: 40
<212> TYPE: DNA
<213> ORGANISM: Bacillus subtilis

<400> SEQUENCE: 9
ggtaacgagc ggccataacct accatcacgt atgaacatcg                          40

<210> SEQ ID NO 10
<211> LENGTH: 40
<212> TYPE: DNA
<213> ORGANISM: Bacillus subtilis

<400> SEQUENCE: 10
tggcattcac attgcatctc ctccggcttc ttcaagtgtt                           40

<210> SEQ ID NO 11
<211> LENGTH: 22
<212> TYPE: DNA
<213> ORGANISM: Bacillus subtilis

<400> SEQUENCE: 11
catgtgaagt tccaatacct gc                                              22

<210> SEQ ID NO 12
<211> LENGTH: 19
<212> TYPE: DNA
<213> ORGANISM: Bacillus subtilis

<400> SEQUENCE: 12
gcgagaagag gatgtctgg                                                  19
```

SYSTEM AND METHOD FOR IMMOBILIZATION FREE ELECTROCHEMILUMINESCENCE DNA DETECTION USING A LUMINOPHORE DYE FOR MULTI-SPECIES DETECTION

RELATED APPLICATION

This application claims the benefit of Brunei Application No. BN/N/2016/0064 filed on Aug. 8, 2016 and entitled "System and Method for Immobilization free electrochemiluminescence DNA detection using a luminophore dye for multi-species detection", the content of which is incorporated in its entirety herein by reference.

BACKGROUND

Technical Field

Present invention related to a novel method for detecting and quantifying target DNA from the biological sample. It provides a method of amplification of DNA sequences with loop-mediated isothermal amplification (LAMP) and its easy and accurate detection and quantification by electrochemiluminescence (ECL) technique which give sequence-specific DNA detection from different biological samples at picogram levels. The present invention finds application in variety of fields including food testing, life science research, medical diagnostics etc.

Description of the Related Art

There are various methods known for the amplification of DNA from a biological sample. In each case the DNA is first extracted and then purified before subjecting to amplification. Most of nucleic acid detection assays are difficult to perform and requires bulky and costly equipment with huge amounts of reagent usage. For example, polymerase chain reaction (PCR) requires three different thermal cycling, electrophoresis post processing or fluorescent labelling, which takes much more time to accomplish the whole detection process. All these limitations, have led nucleic acid amplification toward removing thermal cycling and performing amplification isothermally. In this regard, loop-mediated isothermal amplification (LAMP) provides one of the available alternatives.

LAMP amplicon was detected utilizing turbidity, electrochemical, gel electrophoresis, fluorescence, lateral flow test and magnetic beads. All these detection modalities have a major drawback in providing significant difference between positive and negative samples, which yields difficulties in quantitative analysis of nucleic acids. Consequently, there remains a long-felt need for an effective and easy process for detecting and quantifying target DNA from the biological sample.

SUMMARY

The present invention provides a method for detecting and quantifying target DNA from the biological sample. The method involves first subjecting the biological sample to DNA extraction and then subjecting the obtained DNA sequence to amplification using one or more primers suitable for amplification of target DNA by loop-mediated isothermal amplification method. The obtained DNA amplicons are then provided for electrochemiluminescence detection technique by adding said DNA amplicons in one of the at least two reaction cells containing a luminophore on a carbon electrode surface in an aqueous buffer solution and thereon adding electrochemiluminescence reaction triggering reagent to the reaction cells. The detection and quantification of the target DNA is accomplished by comparing the difference between the intensities of light transmitted from the cells.

As used herein, the term "biological sample" means a sample obtained from an animal or microbial species for detection of target animal or microbial DNA. It includes meat samples and the preserved genomic DNA samples. In the method of this aspect of the present invention, the luminophore is a chemical compound capable to exhibit luminescent properties. The aqueous buffer solution referred hereinabove facilitates the electrochemical reaction to produce light in the cells.

Preferably, in this aspect of the present invention, the setting up of electrochemiluminescence detection technique for detection and quantification of target DNA include the sub-steps of: preparing two or more reaction cells by binding a luminophore on a carbon electrode surface in an aqueous buffer solution. The obtained DNA amplicons are added in one of the cells followed by adding electrochemiluminescence reaction triggering reagent to the reaction cells. The transmitted light intensities from the reaction cells are measured and compared. The difference between the intensities of light transmitted from the reaction cells interprets the presence of target DNA in biological sample. The quantitation of intensity difference is co-related with the quantity of the target DNA.

According to a second aspect of the present invention, there is provided a method for detecting and quantifying target DNA of *Sus scrofa* species from the biological sample. It includes first subjecting the biological sample to DNA extraction and then subjecting the obtained DNA sequence to amplification using one or more primers suitable for amplification of target DNA of *Sus scrofa* species by loop-mediated isothermal amplification method. The obtained DNA amplicons are then provided for electrochemiluminescence detection technique by adding said DNA amplicons in one of the at least two reaction cells containing a luminophore on a carbon electrode surface in an aqueous buffer solution and thereon adding electrochemiluminescence reaction triggering reagent to the reaction cells. The detection and quantification of the target DNA of *Sus scrofa* species is accomplished by comparing the difference between the intensities of light transmitted from the cells.

And also provided a set of primers suitable for amplification of target DNA of *Sus scrofa* species. More preferably in include the primers identified by SEQ ID NO:1, SEQ ID NO:2, SEQ ID NO:3, SEQ ID NO:4, SEQ ID NO:5 and SEQ ID NO:6 in the description.

According to a third aspect of the present invention, there is provided a method for detecting and quantifying target DNA of *Bacillus subtilis* species from the biological sample. It includes first subjecting the biological sample to DNA extraction and then subjecting the obtained DNA sequence to amplification using one or more primers suitable for amplification of target DNA of *Bacillus subtilis* species by loop-mediated isothermal amplification method. The obtained DNA amplicons are then provided for electrochemiluminescence detection technique by adding said DNA amplicons in one of the at least two reaction cells containing a luminophore on a carbon electrode surface in an aqueous buffer solution and thereon adding electrochemiluminescence reaction triggering reagent to the reaction cells. The detection and quantification of the target DNA of Bacillus subtilis species is accomplished by comparing the difference between the intensities of light transmitted from the cells.

And also provided a set of primers suitable for amplification of target DNA of Bacillus subtilis species. More preferably in include the primers identified by SEQ ID NO:7, SEQ ID NO:8, SEQ ID NO:9, SEQ ID NO:10, SEQ ID NO:11, SEQ ID NO:12 in the description.

According to a fourth aspect of the present invention, there is provided a kit for use in the methods set forth in second and third aspects, which include the suitable primers; the luminophore; the buffer reagent in dry form and water for making its aqueous solution, or in the form of already prepared aqueous buffer solution; two or more reaction cells transmitting the light generated in electrochemiluminescence reactions only through their specific portions; and the electrochemiluminescence reaction triggering reagent.

Preferably, in the method of second and third aspect of the present invention, the luminophore is Tris(2, 2'-bipyridyl)dichlororuthenium(II) hexahydrate ([Ru(bpy)$_3$]Cl$_2$), the buffer is Tris-EDTA, and the electrochemiluminescence reaction triggering reagent is tripropylamine. The reaction cells are tubular bottles completely shielded with a silver-mirror film except the base to allow the transmission of light.

As above, all the aspect of the present invention can provide a highly sensitive strategy for the detection of sequence-specific DNA from different biological samples at picogram levels.

These aspects of the present invention will be better appreciated and understood when considered in conjunction with the following description and the accompanying figures. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE FIGURES

The embodiments herein will be better understood from the following detailed description with reference to the drawings, in which.

DETAILED DESCRIPTION OF PREFERRED EMBODIMENTS

Figure 1:
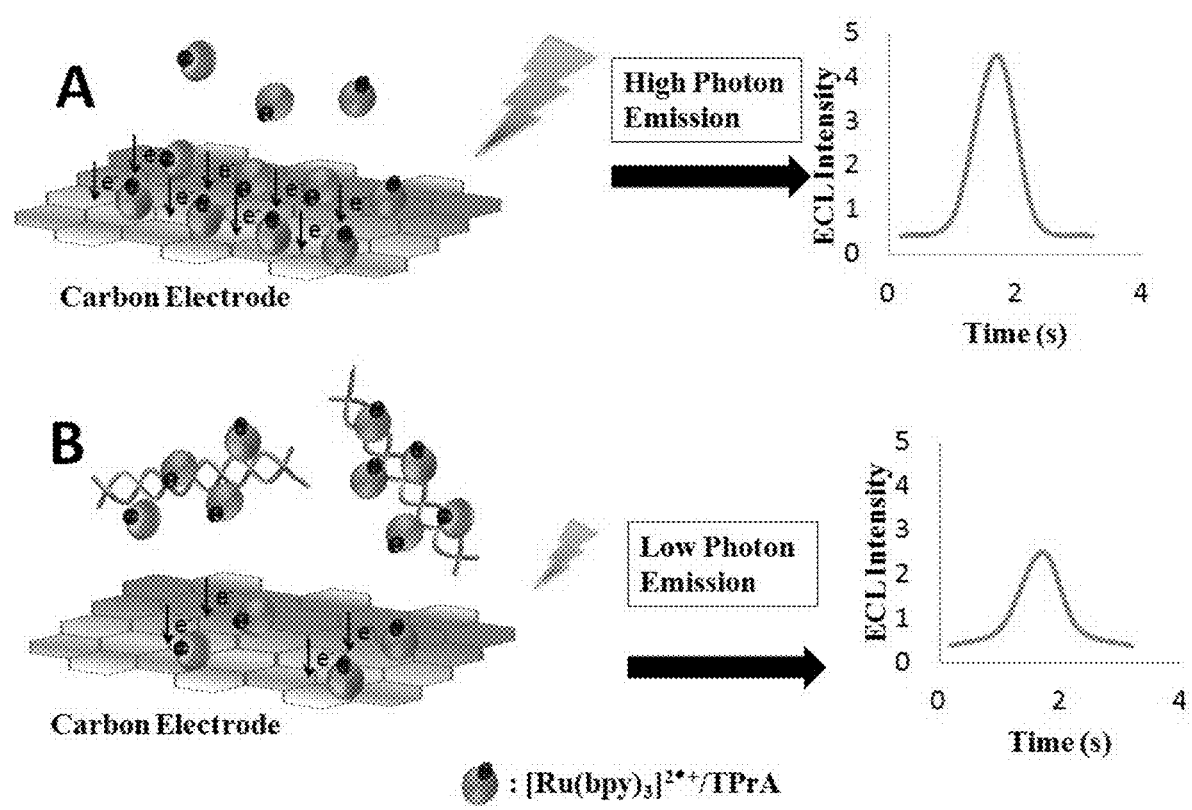
FIG. 1 is the illustration of the immobilization free mechanism of the LAMP-ECL system in the presence or absence of DNA according to an embodiment mentioned herein. In absence of dsDNA, [Ru(bpy)$_3$]Cl$_2$ and TPrA emit high ECL intensities on the surface of the carbon electrodes as seen in A and when dsDNA strands are produced by the LAMP reaction these DNA molecules bind to [Ru(bpy)3]Cl2 and TPrA in solution, resulting in lower photon emission and lower ECL intensity being detected as seen in B.

As mentioned, there remains a long-felt need for an effective and easy process for detecting and quantifying target DNA from the biological sample. The present embodiment enables to address this long-felt need.

Variety of biological samples originating from variety of animals, plants, and micro-organisms even from different geographies can be analyzed for the detection and quantitation of the target DNA in accordance with the present invention.

In the method of present invention, the biological sample is first subjected to DNA extraction using any of the available conventional methods. The obtained DNA sequence is then subjected to amplification by LAMP method using the primers suitable for amplification of target DNA. The suitability of these primers depends on their specificity for the target DNA. The obtained DNA amplicons are then exposed to ECL technique.

In ECL technique two or more reaction cells are prepared by binding a luminophore on a carbon electrode surface in an aqueous buffer solution. All reaction cells are completely shielded with a light reflector material except at certain specific area which allows transmission of light for measuring its intensity. One of the reaction cells is added with the obtained DNA amplicons. After which all the reaction cells are added with the ECL reaction triggering reagent which triggers the electrochemical reaction to yield luminescence.

If the target DNA is present in the pool of amplicons, then it bound electrostatically with a luminophore through electrostatic interactions at the carbon electrode surface, these complexes result in slower diffusion on the carbon electrode surface resulting in decreased ECL signal. It effects in decrease in the intensity measured for the light transmitted through that reaction cell compared to the intensity measured for other reaction cells.

The transmitted light intensities from the reaction cells are measured and compared. The difference between the intensities of light transmitted from the reaction cells interprets the presence of target DNA in biological sample. The quantitation of intensity difference is co-related with the quantity of the target DNA. The method provides a new and highly sensitive strategy for the detection of sequence-specific DNA from different biological samples at picogram levels. The target DNA of Sus scrofa (pork) meat was detected as low as 1 pg/µL ($3.43 \times 10^{-1}$ copies/µL) and for Bacillus subtilis DNA samples the detection limit of 10 pg/µL ($2.2 \times 10^3$ copies/µL) was achieved.

This method has shown to detect LAMP amplicon from the 11.3 min of amplification, with less than 1 min of incubation with [Ru(bpy)$_3$]Cl$_2$-TPrA and a few seconds of scanning with the ECL sensor required for detection of these amplicon, in contrast with the 60 minutes total required for other combinations of amplification and post-amplification detection strategies. The simplicity of the LAMP method and the easy fabrication of the ECL system combined hold significant potential for incorporation into point-of-care devices for food and clinical safety in low-resource areas, which could incorporate chip types constructed from different materials such as paper and plastics to make it even more cost-effective.

Overall, the main advantage of the system described here is the faster detection, minimal instruments and consumption of less reagents. The method of current invention provides robust quantification of nucleic acids.

The advantages of being isothermal, sensitive and robust with ability for multiplex detection of bio-analytes makes this method a facile and appealing sensing modality in hand-held devices to be used at the point-of-care (POC). Fast, sensitive, specific, easy-to-operate assays combined with the miniaturization of instruments have become increasingly important in research and current invention can fulfil all these requirements making this system ideal for incorporation in POC devices for various applications. Further, this method has significant potential for developing a reusable on-site DNA detection platform.

EXAMPLES

The exemplary embodiment of the present invention will be more specifically described by showing an example below. It is understood that the present invention is not limited to the following examples.

Chemicals and Materials

Tris(2,2'-bipyridyl)dichlororuthenium(II) hexahydrate ([Ru(bpy)$_3$]Cl$_2$) and tripropylamine (98% purity) were purchased from Sigma-Aldrich (Bejing, China). For all experiments, samples were diluted with 5 mM TE (Tris-EDTA) buffer, pH 7.5. The same buffer was used for electrochemical detection, LAMP reactions and washing the electrodes. ECL measurements were performed in 5 mM TE buffer (pH 8.0) containing 1 M Tris-HCl and 0.5 M EDTA.

LAMP reactions for *Sus scrofa* and *Bacillus subtilis* were performed in polypropylene tubes in a 25 µL reaction volume with a 1× reaction mix comprising 6 mM MgSO$_4$ (New England Biolabs, Mass., USA), 0.4 mM dNTPs (New England Biolabs), 0.64 M betaine (Sigma-Aldrich), 0.2 µM each of the forward outer and reverse outer primers (all primers sourced from Integrated DNA Technologies, Coralville, Iowa, USA), 1.6 µM each of the forward inner and reverse inner primers, 0.8 µM each of the loop forward and loop reverse primers, 16 U of the Bst (*Bacillus stearothermophilus*) DNA polymerase large fragment (New England Biolabs), 2.5 µL of 10× ThermoPol buffer (New England Biolabs) and 5 µL of genomic DNA. All reagents were of analytical grade and used as received. All aqueous solutions were prepared using ultrapure water (specific resistance of 18.0 Me-cm).

The LAMP amplification temperature was optimized, by testing amplification at 60° C., 63° C. and 65° C. It was observed that for *S. scrofa*, optimal LAMP amplification occurred at 65° C. whereas 63° C. was optimal for *B. subtilis*. Betaine was optimized from 0.4 to 1.4 M, dNTPs from 0.4 to 1.4 mM, and MgSO$_4$ from 3 to 8 mM. Optimal results for the pork samples were obtained with betaine at 1.4 M, dNTPs at 1.4 mM and MgSO$_4$ at 6 mM. For the *Bacillus* samples, optimal results were obtained with betaine at 0.64 M, dNTPs at 0.4 mM and MgSO$_4$ at 3 mM.

Apparatus and Methods

An MPI-A Capillary Electrophoresis Electrochemiluminescence Analyzer system was purchased from Xi'an Yima Opto-Electrical Technology Co., Ltd. A working ECL cell was used to receive the light emitted from the ECL reactions and to conduct it to an ultra-sensitive single photon-counting module or photomultiplier tube (PMT). To collect the light emission, the electrode was immersed inside the ECL cell containing the reaction mixture and mounted over the PMT. MPI-A software was used for ECL analysis. The disposable carbon electrochemical printed chip electrodes used in the ECL detection process were purchased from BioDevice Technology. The electrodes were prepared on a plastic substrate with the dimensions 12.5×4×2 (LWH) and the electrodes required 20-30 µL of the sample solution for complete immersion.

Post LAMP amplification, the amplicons were analysed with 2% agarose gel electrophoresis where typical LAMP ladder-like patterns were obtained. The detection of the LAMP products using the ECL-based method was then investigated. Different concentrations of DNA template were amplified and analyzed by LAMP, and then at the same time measured ECL intensity upto 60 min for quantitative detection of *Sus scrofa* and *Bacillus subtilis* target DNA.

EXAMPLE 1

DNA Preparation and Collection for *Sus scrofa* Species

Pork meat samples were collected from different markets with different origins and following genomic DNA extraction with the DNeasy tissue kit (Qiagen, Germany), the purified DNA concentrations were measured with a Nano-Photometer (Implen GmbH, Germany) and these samples were then stored at −20° C. until further use.

Primers and Preparation of LAMP Reactions for *Sus scrofa* Species

Optimized primer set for *Sus scrofa* which comprise regions of the Cytochrome b gene (GenBank accession #AFO34253.1) was used in LAMP reaction. Table 1 below gives the details of those optimized primers identified as SEQ ID NO:1 to SEQ ID NO:6. LAMP reactions were carried out at temperatures ranging from 60° C. to 65° C. and for different time periods of up to 60 min (ST 1 in Supplementary information). The total volume of the LAMP reaction was 25 mL and 5 mL of gDNA template was added to reaction. To avoid evaporation, 10 mL of mineral oil was used to overlay the reaction solution. The gels were run at 80 V for 2 h and subsequently viewed with an Ultra Violet Product (UVP machine, Upland, Calif., USA).

TABLE 1

Primer details

| SEQ | Type | Sequence |
|---|---|---|
| SEQ ID NO. 1 | Forward outer | 5'-TCGCCTACGCTATTCTAC-3' |
| SEQ ID NO. 2 | Reverse outer | 5'-GGAAGTATAAGATGGAGGCTA-3' |
| SEQ ID NO. 3 | Forward inner | 5'-GGATGTGTGTAGTATGGGCATTAACTAGGTGGAGTGTTGG-3' |
| SEQ ID NO. 4 | Reverse inner | 5'-TTCGACCACTAAGTCAATGCCGGTTGTCCTCCAATTCATG-3' |
| SEQ ID NO. 5 | Loop forward | 5'-ATTAGGATTAGGATGGAGGCTA-3' |
| SEQ ID NO. 6 | Loop reverse | 5'-CTAGTAGCAGACCTCATTACAC-3' |

ECL Detection:

For the analysis of the LAMP samples, 5 mL of LAMP amplicon, 100 mL of [Ru(bpy)$_3$]Cl$_2$ and 100 mL of TPrA were added in TE buffer having pH 7.5. This mixture was placed in an ECL cell comprising a 2 mL tubular bottle completely shielded with a silver-mirror film, leaving only the base (diameter 0.8 cm) to allow the transmission of light. The ECL cell was placed above the center of a PMT, which detected the ECL intensity while the rest of the cell was shielded in a black box.

Figure 2:
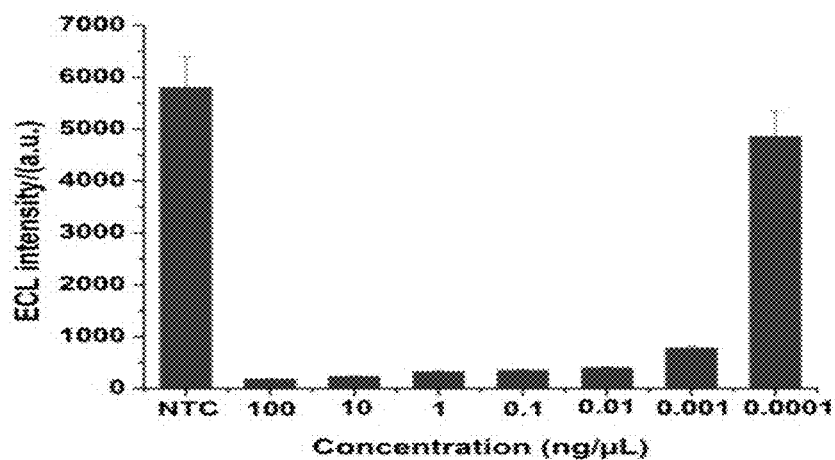
FIG. 2 is the illustration of the ECL detections of LAMP amplicon produced with Sus scrofa loop primers for determining the limit of detection of the LAMP-ECL assay for pork species of LAMP DNA. NTC denotes a negative control containing no DNA.

The LAMP reactions were performed with 100-0.0001 ng/mL of pork genomic DNA to determine the lowest limit of detection obtainable using this method. The limit of detection for pork species was observed to be 1 pg/mL as seen in FIG. 2.

EXAMPLE 2

DNA Preparation and Collection for *Bacillus subtilis* Species

The *Bacillus subtilis* genomic DNA was obtained from the Leibniz Institute (DSMZ, Germany) and stored at −20° C.

Primers and Preparation of LAMP Reactions for *Bacillus subtilis* Species

Optimized primer set for *Bacillus subtilis* which comprise regions of the rpoB gene (GenBank accession #NC_000964.3) was used in LAMP reaction. Table 2 below gives the details of those optimized primers identified as SEQ ID NO:7 to SEQ ID NO:12. LAMP reactions were carried out in similar manner including similar temperature and time as mentioned in example 1 above.

TABLE 2

Primer details

| SEQ | Type | Sequence |
|---|---|---|
| SEQ ID NO. 7 | Forward outer | 5'-GAAGAGGATATGCCTTACCTTC-3' |
| SEQ ID NO. 8 | Reverse outer | 5'-CGACAGATACACGGTTATCAA-3' |
| SEQ ID NO. 9 | Forward inner | 5'-GGTAACGAGCGGCCATACCTACCATCACGTATGAACATCG-3' |
| SEQ ID NO. 10 | Reverse inner | 5'-TGGCATTCACATTGCATCTCCTCCGGCTTCTTCAAGTGTT-3' |
| SEQ ID NO. 11 | Loop forward | 5'-CATGTGAAGTTCCAATACCTGC-3' |
| SEQ ID NO. 12 | Loop reverse | 5'-GCGAGAAGAGGATGTCTGG-3' |

ECL Detection:

The analysis of the LAMP samples was carried out in similar manner as mentioned in example 1 above.

Figure 3:
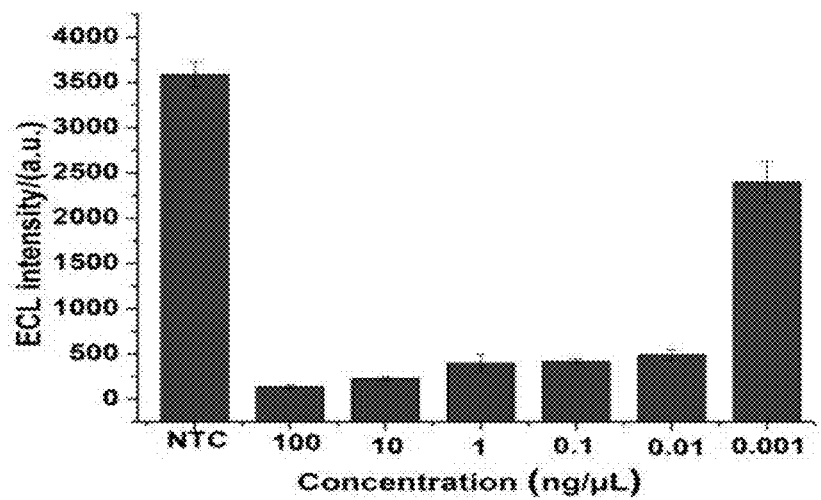
FIG. 3 is the illustration of the ECL detections of LAMP amplicon produced with Bacillus subtilis loop primers for determining the limit of detection of the LAMP-ECL assay for Bacillus subtilis species of LAMP DNA. NTC denotes a negative control containing no DNA.

The LAMP reactions were performed with 100-0.0001 ng/mL of *Bacillus* input genomic DNA to determine the lowest limit of detection obtainable using this method. The limit of detection for *Bacillus subtilis* species was observed to be 10 pg/mL as seen in FIG. 3.

EXAMPLE 3

Checking Specificity of the Lamp-ECL System

Figure 4:
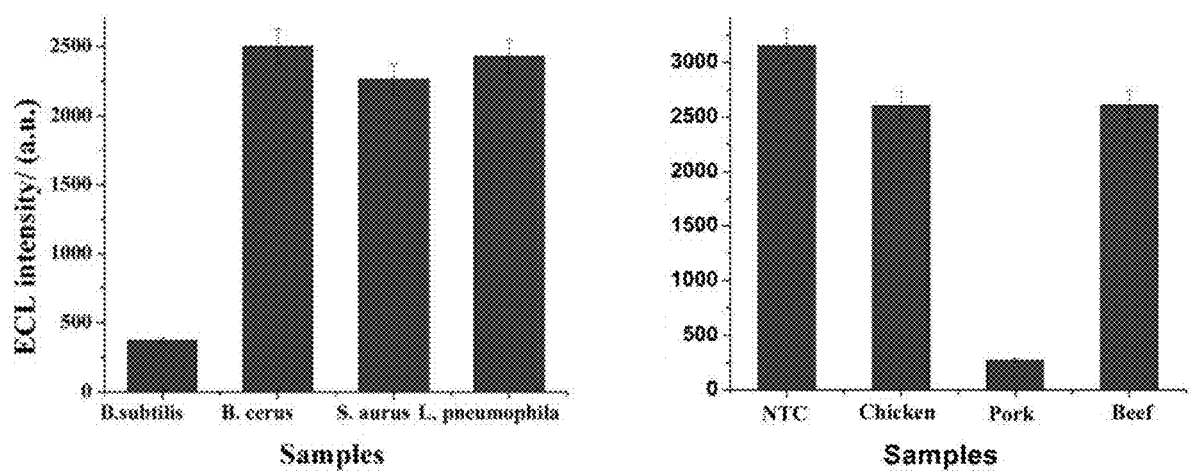
FIG. 4 illustrates the results of cross-reactivity test of Sus scrofa and Bacillus subtilis primers according to an embodiment mentioned herein. The cross-reactivity of the pork primers was measured for the negative control (NTC) and chicken, pork (positive control) and beef genomic DNA as seen in A and the ross-reactivity of the Bacillus subtilis primers was measured for Bacillus subtilis (positive control), Bacillus cereus, Staphylococcus aureus and Legionella pneumophila genomic DNA as seen in B.

To check for species cross-reactivity, the LAMP assays for both species namely *Sus scrofa* and *Bacillus subtilis* were tested with genomic DNA input from various other species. As seen in FIG. 4 and tables 3 and 4 below, it was observed that in both cases the loop primers did not cross-react with other species' genomic DNA. A DNA template input concentration of 10 pg/mL was used for all cross-reactivity experiments.

TABLE 3

| Sample no. | Sample type | Species as labelled | Detection of DNA with pork-specific LAMP-ECL | Average ECL intensity (a.u.) | SD |
|---|---|---|---|---|---|
| 1 | Spiced pork cubes | *Sus scrofa* | Yes | 357 | 48.32 |
| 2 | Pork mince with bean paste | *Sus scrofa* | Yes | 448 | 9.93 |
| 3 | Chopped pork & ham | *Sus scrofa* | Yes | 368.50 | 32.27 |
| 4 | Chao San Si (pork & bamboo shoot) | *Sus scrofa* | Yes | 541 | 37.26 |
| 5 | Mutton luncheon with chicken | *Gallus gallus*, *Puffinus tenuirostris* | No | 1821.50 | 111.94 |
| 6 | Corned beef | *Bos taurus* | No | 1802.52 | 40.869 |
| 7 | Chicken luncheon meat | *Gallus gallus* | No | 2247.20 | 321.38 |
| 8 | Beef loaf | *Bos taurus* | No | 1310.22 | 72.75 |
| 9 | Chicken luncheon meat | *Gallus gallus* | No | 1677.70 | 82.37 |
| 10 | Mallow bakes | *Bos taurus* | No | 1742.24 | 30.78 |
| 11 | Chamallows | *Bos taurus* | No | 1154.71 | 37.17 |
| 12 | Marshmallows | *Bos taurus* | No | 1267.70 | 22.03 |
| 13 | Boar meat | *Sus scrofa* | Yes | 529.54 | 11.09 |
| 14 | Corned mutton | *Puffinus tenuirostris* | No | 1439.20 | 43.19 |
| 15 | Chicken luncheon meat | *Gallus gallus* | No | 1263.71 | 27.80 |
| 16 | Curry beef | *Bos taurus* | No | 1545 | 20.99 |
| 17 | Chicken luncheon meat | *Gallus gallus* | No | 1790 | 81.47 |
| 18 | Corned ostrich | *Struthio camelus* | No | 1137.23 | 269.01 |
| 19 | Lamb curry with potatoes | *Ovis aries* | No | 1106 | 108.76 |
| 20 | Duck meat | *Anas platyrhynchos* | No | 1561.70 | 46.18 |
| 21 | Canned beef luncheon meat | *Bos taurus* | No | 1828.70 | 70.64 |
| 22 | Sliced ham | *Sus scrofa* | Yes | 646 | 34.38 |

TABLE 4

| Samples | Species as labelled | Detection of pork with ECL sensor | Average ECL intensity (a.u.) | SD |
|---|---|---|---|---|
| Pork | *Sus scrofa* | Yes | 431.75 | 21.58 |
| Wild boar | *Sus scrofa* | Yes | 350.55 | 17.52 |
| Sheep | *Ovis aries* | No | 2653 | 132.65 |
| Ostrich | *Struthio camelus* | No | 2627.25 | 132.86 |
| Goat | *Capra aegagrus phircus* | No | 2717.75 | 135.88 |
| Turkey | *Meleagris gallopavo* | No | 2786 | 139.36 |
| Buffalo | *Bison bison* | No | 3088.54 | 154.42 |
| Horse | *Equus caballus* | No | 2485.25 | 124.26 |
| Duck | *Anas platyrhynchos* | No | 2576.75 | 128.83 |

EXAMPLE 4

Checking Specificity of the Lamp-ECL System

Figure 5:
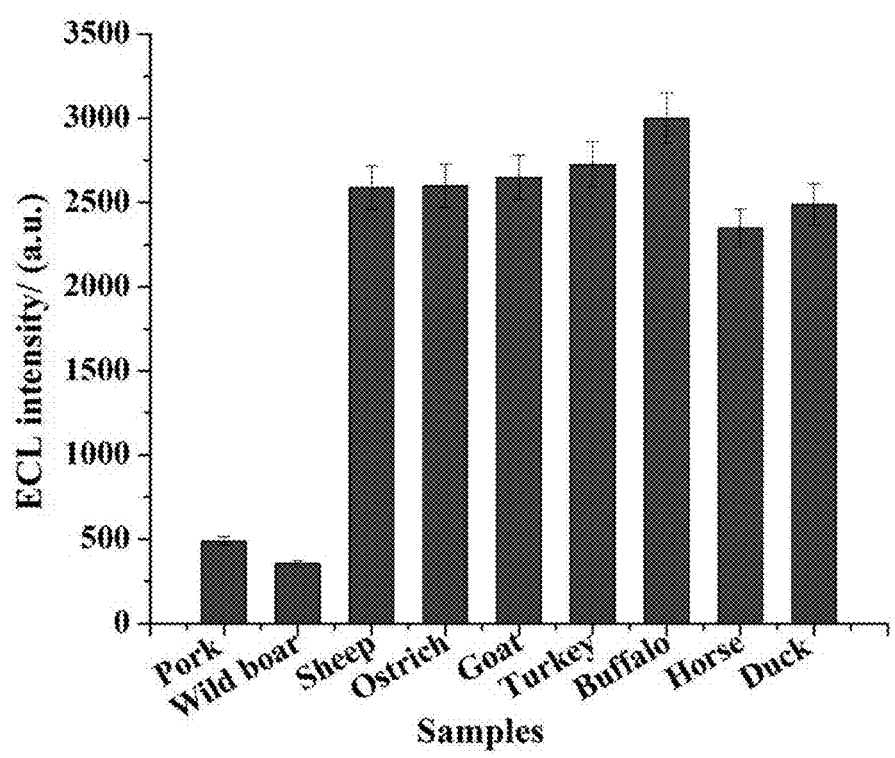
FIG. 5 is the graphical illustration of the specificity of the LAMP-ECL system using sample genomic DNA from the meat of various species.

ECL analysis of nine different meat samples was performed. LAMP amplifications were performed with sample genomic DNA and pork-specific loop primers. Pork and wild boar showed positive amplifications giving low ECL intensities whereas the other non-pork species showed negative results giving high ECL intensities as seen in FIG. 5.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope.

What is claimed:

1. A method of detecting and quantifying target DNA from a biological sample comprising:
   subjecting the biological sample to DNA extraction and subjecting the obtained DNA sequence to amplification using one or more primers for amplification of target DNA by loop-mediated isothermal amplification (LAMP) method, wherein the one or more primers are selected from a group of twelve primers based on specificity for the target DNA, wherein the group includes a first group of six primers for a target DNA of *Sus scrofa* species and a second group of six primers for a target DNA of *Bacillus subtilis* species;

obtaining DNA amplicons based on the amplification of the target DNA by the LAMP method using the selected one or more primers;

subjecting the obtained DNA amplicons to a 1-10 picogram/mL level electrochemiluminescence detection technique by binding the obtained DNA amplicons in one of at least two reaction cells containing a luminophore $[Ru(bpy)_3]Cl_2$ on a carbon electrode surface in an aqueous buffer solution;

adding electrochemiluminescence reaction triggering reagent to the reaction cells to obtain a mixture of the DNA amplicons, luminophore $[Ru(bpy)_3]Cl_2$, aqueous buffer solution, and electrochemiluminescence reaction triggering reagent; and comparing difference between intensities of light transmitted from the reaction cells to detect and quantify the target DNA, wherein a quantity of the target DNA is based on quantitation of difference between the intensities, wherein intensity of light transmitted from the reaction cell with presence target DNA is less than intensity of light transmitted from a reaction cell with absence of the target DNA.

2. A method of detecting and quantifying target DNA of *Sus scrofa* species from a biological sample comprising:

subjecting the biological sample to DNA extraction and subjecting the obtained DNA sequence to amplification using one or more of six primers suitable for amplification of target DNA of *Sus scrofa* species by loop-mediated isothermal amplification method, wherein the target DNA of *Sus scrofa* species is amplified using the one or more of six primers selected based on specificity for the target DNA of *Sus scrofa* species, wherein the one or more of six primers do not cross react with other species' genomic DNA;

subjecting the obtained DNA amplicons to electrochemiluminescence detection technique by adding said DNA amplicons in one of at least two reaction cells containing a luminophore on a carbon electrode surface in an aqueous buffer solution;

adding electrochemiluminescence reaction triggering reagent to the reaction cells; and comparing difference between intensities of light transmitted from the reaction cells to detect and quantify the target DNA of *Sus scrofa* species, wherein detection limit for the target DNA of *Sus scrofa* is 1 pg/µL.

3. The method of claim 2, wherein the primer is selected from the group consisting of SEQ ID NO: 1, SEQ ID NO: 3, SEQ ID NO: 4, SEQ ID NO: 5, SEQ ID NO:6 and any combination thereof, wherein the selected primer is being used in LAMP reactions at a temperature range of 60° C. to 65° C.

4. The method of claim 2, wherein the luminophore is $[Ru(bpy)3]Cl2$.

5. The method of claim 2, wherein the aqueous buffer solution has pH 7.5 and made by preparing aqueous solution of Tris-EDTA.

6. The method of claim 2, wherein the electrochemiluminescence reaction triggering reagent is tripropylamine, wherein a mixture is obtained by mixing the DNA amplicons, luminophore $[Ru(bpy)_3]Cl_2$, the aqueous buffer solution having pH 7.5 and made by preparing aqueous solution of Tris-EDTA, and the electrochemiluminescence reaction triggering reagent.

7. The method of claim 2, wherein the difference between the intensities of light transmitted from the cells is compared after 15 minutes of amplification.

8. The method of claim 2, wherein the reaction cells include a 2 ml tubular bottle completely shielded with a silver-mirror film except the base to allow the transmission of light, wherein the reaction cells containing a mixture of LAMP amplicon, luminophore, and TE buffer having pH of 7.5 are placed above center of a photomultiplier tube.

9. A method of detecting and quantifying target DNA of *Bacillus subtilis* species from the biological sample comprising:

subjecting the biological sample to DNA extraction and subjecting the obtained DNA sequence to amplification using one or more of six primers suitable for amplification of target DNA of *Bacillus subtilis* species by loop-mediated isothermal amplification method, wherein each of the six primers is of different type;

obtaining DNA amplicons based on optimal amplification of the target DNA by the LAMP method using the selected one or more primers at a temperature of 63° C. optimal for *Bacillus subtilis* species;

subjecting the obtained DNA amplicons to electrochemiluminescence detection technique by adding said DNA amplicons in one of the at least two reaction cells containing a luminophore on a carbon electrode surface in an aqueous buffer solution;

ading electrochemiluminescence reaction triggering reagent to the reaction cells; and comparing the difference between the intensities of light transmitted from the cells to detect and quantify the target DNA of *Bacillus subtilis* species.

10. The method of claim 9, wherein the primer is selected from the group consisting of SEQ ID NO:9, SEQ ID NO:10, SEQ ID NO:11, SEQ ID NO:12 and any combination thereof.

11. The method of claim 9, wherein the luminophore is $[Ru(bpy)_3]Cl_2$.

12. The method of claim 9, wherein the aqueous buffer solution has pH 7.5 and made by preparing aqueous solution of Tris-EDTA.

13. The method of claim 9, wherein the electrochemiluminescence reaction triggering reagent is tripropylamine.

14. The method of claim 9, wherein the difference between the intensities of light transmitted from the cells is compared after 15 minutes.

15. The method of claim 9, where the reaction cells include tubular bottle completely shielded with a silver-mirror film except the base to allow the transmission of light.

* * * * *